United States Patent [19]

Ho et al.

[11] Patent Number: 6,084,112

[45] Date of Patent: Jul. 4, 2000

[54] METHOD FOR PREPARING ω-AMINOALKANOIC ACID DERIVATIVES FROM CYCLOALKANONES

[75] Inventors: Koc-Kan Ho, Mount Kisco, N.Y.; Andrea Leone-Bay, Ridgefield, Conn.

[73] Assignee: Emisphere Technologies, Inc., Tarrytown, N.Y.

[21] Appl. No.: 08/894,490

[22] PCT Filed: Sep. 10, 1996

[86] PCT No.: PCT/US96/14805

§ 371 Date: Dec. 16, 1997

§ 102(e) Date: Dec. 16, 1997

[87] PCT Pub. No.: WO97/10197

PCT Pub. Date: Mar. 20, 1997

Related U.S. Application Data

[60] Provisional application No. 60/003,508, Sep. 11, 1995.

[51] Int. Cl.⁷ ............................................... C07C 227/00
[52] U.S. Cl. .......................................................... 554/114
[58] Field of Search ............................................. 584/114

[56] References Cited

U.S. PATENT DOCUMENTS

| | | |
|---|---|---|
| Re. 24,899 | 11/1960 | Green . |
| 2,671,451 | 3/1954 | Bolger ..................................... 128/260 |
| 2,828,206 | 3/1958 | Rosenberg ..................................... 99/2 |
| 2,862,918 | 12/1958 | Meyer et al. ........................ 260/123.5 |
| 2,868,740 | 1/1959 | Luce ............................................ 260/8 |
| 2,971,916 | 2/1961 | Schleicher et al. .................... 252/62.5 |
| 3,016,308 | 1/1962 | Macaulay .................................. 177/37 |
| 3,052,655 | 9/1962 | Fox et al. .................................. 260/78 |
| 3,057,344 | 10/1962 | Abella et al. ............................... 128/2 |
| 3,076,790 | 2/1963 | Fox et al. .................................. 260/78 |
| 3,170,802 | 2/1965 | Fukushima ................................ 99/145 |
| 3,190,837 | 6/1965 | Brynko et al. ........................... 252/316 |
| 3,474,777 | 10/1969 | Figge et al. ................................ 128/2 |
| 3,491,093 | 1/1970 | Pachter et al. ....................... 260/247.5 |
| 3,565,559 | 2/1971 | Sato ......................................... 424/37 |
| 3,567,650 | 3/1971 | Bakan .................................... 252/316 |
| 3,574,832 | 4/1971 | Engel et al. ............................ 424/183 |
| 3,576,758 | 4/1971 | Emrick .................................. 252/316 |
| 3,687,926 | 8/1972 | Arima et al. ........................ 260/112.5 |
| 3,725,113 | 4/1973 | Chang ...................................... 117/82 |
| 3,748,277 | 7/1973 | Wagner .................................. 252/316 |
| 3,794,561 | 2/1974 | Matsukawa et al. ................. 195/29 R |
| 3,795,739 | 3/1974 | Birkmayer et al. .................... 424/274 |
| 3,816,404 | 6/1974 | Kablaoui et al. .................... 260/239.3 |
| 3,822,348 | 7/1974 | Higashi et al. ........................... 424/95 |
| 3,849,550 | 11/1974 | Teitelbaum ............................... 424/78 |
| 3,933,873 | 1/1976 | Love et al. ........................... 260/239.3 |
| 3,937,668 | 2/1976 | Zolle ..................................... 252/316 |
| 3,939,253 | 2/1976 | Bodor et al. ........................... 424/309 |
| 3,956,172 | 5/1976 | Saeki et al. ........................... 252/316 |
| 3,962,416 | 6/1976 | Katzen ..................................... 424/19 |
| 3,976,773 | 8/1976 | Curran ................................... 424/250 |
| 4,035,507 | 7/1977 | Bodor et al. ........................... 424/311 |
| 4,048,268 | 9/1977 | Ludwig ..................................... 264/15 |
| 4,061,466 | 12/1977 | Sjoholm et al. ..................... 23/230 B |
| 4,117,801 | 10/1978 | Dannelly et al. ......................... 118/20 |

(List continued on next page.)

FOREIGN PATENT DOCUMENTS

| | | |
|---|---|---|
| 1077842 | 8/1976 | Canada ............................. A61K 9/50 |
| 0 000 667 A1 | 2/1979 | European Pat. Off. ......... A61K 9/50 |
| 0 036 145 A1 | 9/1981 | European Pat. Off. ....... A61K 31/62 |
| 0 068 314 | 1/1983 | European Pat. Off. ....... A61K 31/16 |
| 0 105 804 | 4/1984 | European Pat. Off. ........ C12N 15/00 |
| 0 130 162 A2 | 1/1985 | European Pat. Off. ......... B01J 13/02 |
| 0 342 054 A2 | 11/1989 | European Pat. Off. ......... A61K 7/06 |
| 0 342 056 A2 | 11/1989 | European Pat. Off. ......... A61K 7/06 |
| 0 365 183 | 4/1990 | European Pat. Off. ....... A61K 31/18 |
| 0 366 277 | 5/1990 | European Pat. Off. ....... A61K 9/107 |
| 0 418 642 | 3/1991 | European Pat. Off. ....... A61K 37/30 |
| 0 448 057 | 9/1991 | European Pat. Off. ........ C12P 21/08 |
| 0 452 161 | 10/1991 | European Pat. Off. ......... A61K 7/48 |
| 0 459 795 | 12/1991 | European Pat. Off. ....... A61K 37/02 |
| 0 467 389 | 1/1992 | European Pat. Off. ......... A61K 9/52 |
| 0 490 549 A1 | 6/1992 | European Pat. Off. ....... A61K 47/12 |
| 0 517 211 A1 | 9/1992 | European Pat. Off. ....... A61K 47/12 |
| 0 616 799 A1 | 9/1994 | European Pat. Off. ......... A61K 7/00 |

(List continued on next page.)

OTHER PUBLICATIONS

Airaudo, C.B. et al. (1987) *Journal of Food Science*, vol. 52(6), pp. 1750–1752.

Andini, S. et al. (1975) *Origins of Life*, vol. 6, pp. 147–153.

Brooke, S. 1 et al. (1977) *BioSystems*, vol. 9, pp. 1–22.

Chen et al. (1975) "Evidence for Hemiacetal Formation", *Biochemistry*, vol. 18, No. 5, pp. 921–925.

Davis et al. (1983) "Leucinal Inhibits . . . ", *Pharmacology Biochemistry Behavior*, vol. 19, pp. 791–794.

Dose, K. (1974) *Origins of Life*, vol. 5, pp. 239–252.

Fasman et al. (1964) *Biochemistry*, vol. 3, No. 11, pp. 1665–1674.

Fox, S.W. et al. (1976) *BioSystems*, vol. 8, pp. 40–44.

Fox, S.W. et al., *Molecular Evolution and the Origin of Life*, Maxel Decker, New York (1977).

Fox, S.W. et al. (1968) *Biochim. Biophys. Acta*, vol. 160, pp. 246–249.

Fox, S.W. (1976) *Origins of Life*, vol. 7, pp. 49–68.

Fox, S.W. (1980) *Naturwissenschaften*, vol. 67, pp. 378–383.

Fox, S.W. et al. (1960) *Archives of Biochemistry and Biophysics*, vol. 86, pp. 281–285.

Fox, S.W. et al. (1974) *Origins of Life*, vol. 5, pp. 227–237.

Fox, S.W. (1984) *Origins of Life*, vol. 14, pp. 485–488.

Gol'dovskii, A.M. (1978) *Zhurnal Evolyutsionnoi Biokhimii i Fiziologii*, vol. 14(6), pp. 437–439.

(List continued on next page.)

*Primary Examiner*—Deborah D. Carr
*Attorney, Agent, or Firm*—Darby & Darby

[57] ABSTRACT

A convenient synthetic route to ω-aminoalkanoic acids, N-Boc protected ω-aminoalkanoic acids and Boc-amino acid coupled ω-aminoalkanoic acids is disclosed. The method provides high purity compounds that generally do not require further purification.

7 Claims, No Drawings

U.S. PATENT DOCUMENTS

| | | | |
|---|---|---|---|
| 4,147,767 | 4/1979 | Yapel | 424/22 |
| 4,183,849 | 1/1980 | Hansen | 260/112.7 |
| 4,199,561 | 4/1980 | Roth et al. | 424/32 |
| 4,217,370 | 8/1980 | Rawlings et al. | 426/98 |
| 4,238,506 | 12/1980 | Stach et al. | 424/319 |
| 4,239,635 | 12/1980 | Rieder | 252/34 |
| 4,239,754 | 12/1980 | Sache et al. | 424/183 |
| 4,272,506 | 6/1981 | Schwarzberg | 424/8 |
| 4,289,759 | 9/1981 | Heavner et al. | 424/177 |
| 4,345,588 | 8/1982 | Widder et al. | 128/1.3 |
| 4,348,384 | 9/1982 | Horikoshi et al. | 424/101 |
| 4,351,337 | 9/1982 | Sidman | 128/260 |
| 4,352,883 | 10/1982 | Lim | 435/178 |
| 4,357,259 | 11/1982 | Senyei et al. | 252/316 |
| 4,388,304 | 6/1983 | Nyeki et al. | 424/177 |
| 4,393,192 | 7/1983 | Curatolo et al. | 528/292 |
| 4,402,856 | 9/1983 | Schnoring et al. | 428/402.22 |
| 4,402,968 | 9/1983 | Martin | 424/273 |
| 4,405,598 | 9/1983 | Brown | 424/45 |
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,457,907 | 7/1984 | Porter | 424/7.1 |
| 4,460,563 | 7/1984 | Calanchi | 424/35 |
| 4,462,839 | 7/1984 | McGinley et al. | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,683,092 | 7/1987 | Tsang | 264/4.3 |
| 4,690,786 | 9/1987 | Ninomiya et al. | 264/4.6 |
| 4,692,284 | 9/1987 | Braden | 264/4.3 |
| 4,692,433 | 9/1987 | Hostetler et al. | 514/12 |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,757,066 | 7/1988 | Shiokari et al. | 514/210 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 424/433 |
| 4,878,942 | 11/1989 | Motegi et al. | |
| 4,886,663 | 12/1989 | Houghten | 424/88 |
| 4,895,725 | 1/1990 | Kantor et al. | 424/455 |
| 4,897,444 | 1/1990 | Byrnes et al. | 525/54.1 |
| 4,900,730 | 2/1990 | Miyauchi | 514/12 |
| 4,908,233 | 3/1990 | Takizawa et al. | 427/213.35 |
| 4,919,939 | 4/1990 | Baker | 424/493 |
| 4,925,673 | 5/1990 | Steiner | 424/455 |
| 4,927,928 | 5/1990 | Shroot et al. | |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,019,400 | 5/1991 | Gombotz et al. | 424/497 |
| 5,023,374 | 6/1991 | Simon | 564/152 |
| 5,039,481 | 8/1991 | Pacifici et al. | 422/4 |
| 5,041,291 | 8/1991 | Bader et al. | 424/426 |
| 5,055,300 | 10/1991 | Gupta | 424/409 |
| 5,066,487 | 11/1991 | Morelle et al. | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 424/80 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 424/70 |
| 5,250,236 | 10/1993 | Gasco | 264/4.4 |
| 5,271,934 | 12/1993 | Goldberg et al. | 424/401 |
| 5,271,961 | 12/1993 | Mathiowitz et al. | 427/213.31 |
| 5,278,148 | 1/1994 | Branca et al. | 514/19 |
| 5,310,535 | 5/1994 | Kruper, Jr. et al. | 424/1.53 |
| 5,328,992 | 7/1994 | Peter et al. | 534/116 |
| 5,352,461 | 10/1994 | Feldstein et al. | 424/493 |
| 5,384,133 | 1/1995 | Boyes et al. | 424/501 |
| 5,389,379 | 2/1995 | Chagnon et al. | 424/450 |
| 5,389,379 | 2/1995 | Dirix et al. | 424/451 |
| 5,401,516 | 3/1995 | Milstein et al. | 424/491 |
| 5,418,010 | 5/1995 | Janda et al. | 427/213.31 |
| 5,439,686 | 8/1995 | Desai et al. | 424/451 |
| 5,443,841 | 8/1995 | Milstein et al. | 424/451 |
| 5,447,728 | 9/1995 | Milstein et al. | 424/490 |
| 5,451,410 | 9/1995 | Milstein et al. | 424/490 |
| 5,474,997 | 12/1995 | Gray et al. | 514/252 |
| 5,536,813 | 7/1996 | Charpenel et al. | 530/324 |
| 5,540,939 | 7/1996 | Milstein et al. | 424/491 |
| 5,541,155 | 7/1996 | Leone-Bay et al. | 514/2 |
| 5,578,323 | 11/1996 | Milstein et al. | 424/499 |
| 5,601,846 | 2/1997 | Milstein et al. | 424/499 |
| 5,629,020 | 5/1997 | Leone-Bay et al. | 424/489 |
| 5,643,957 | 7/1997 | Leone-Bay et al. | 514/563 |
| 5,650,386 | 7/1997 | Leone-Bay et al. | 514/2 |
| 5,665,700 | 9/1997 | Cho et al. | 514/2 |
| 5,667,806 | 9/1997 | Kantor | 424/484 |
| 5,693,338 | 12/1997 | Milstein | |
| 5,705,529 | 1/1998 | Matyus et al. | |
| 5,709,861 | 1/1998 | Santiago et al. | |
| 5,714,167 | 2/1998 | Milstein et al. | |
| 5,750,147 | 5/1998 | Kantor | |

FOREIGN PATENT DOCUMENTS

| | | | |
|---|---|---|---|
| 2 133 926 | 12/1972 | France | A61K 27/00 |
| 2 565 102 | 12/1985 | France | A61K 9/52 |
| 2 343 037 | 3/1975 | Germany | |
| 3 202 255 | 10/1982 | Germany | C08L 89/00 |
| 3 612 102 | 10/1986 | Germany | C07K 15/00 |
| 71258 | 12/1987 | Israel | |
| 56-68612 | 6/1981 | Japan | A61K 31/19 |
| 58-35111 | 3/1983 | Japan | A61K 9/66 |
| 6-107682 | 4/1994 | Japan | |
| 929401 | 6/1963 | United Kingdom | |
| 1 075 952 | 8/1967 | United Kingdom | |
| 1 236 885 | 6/1972 | United Kingdom | |
| 1 567 763 | 5/1980 | United Kingdom | A61K 9/22 |
| 2 095 994 | 10/1982 | United Kingdom | A61K 9/00 |
| WO 85/00105 | 1/1985 | WIPO | A61K 9/52 |
| WO 85/00110 | 1/1985 | WIPO | A61K 47/00 |
| WO 85/00809 | 2/1985 | WIPO | C07D 233/64 |
| WO 87/04076 | 7/1987 | WIPO | A61K 45/02 |
| WO 88/01213 | 2/1988 | WIPO | B23B 5/16 |
| WO 92/19263 | 12/1992 | WIPO | A61K 39/00 |
| WO 93/18754 | 9/1993 | WIPO | A61K 9/16 |

| | | | |
|---|---|---|---|
| WO 93/25583 | 12/1993 | WIPO | C07K 15/00 |
| WO 94/11015 | 5/1994 | WIPO | A61K 37/00 |
| WO 94/14420 | 7/1994 | WIPO | A61K 9/16 |
| WO 94/18950 | 9/1994 | WIPO | A61K 9/127 |
| WO 94/18997 | 9/1994 | WIPO | A61K 37/00 |
| WO 94/21234 | 9/1994 | WIPO | A61K 7/00 |
| WO 94/23702 | 10/1994 | WIPO | A61K 9/16 |
| WO 94/23767 | 10/1994 | WIPO | A61L 9/16 |
| WO 94/24291 | 10/1994 | WIPO | A61K 39/015 |
| WO 94/28878 | 12/1994 | WIPO | A61K 9/14 |
| WO 95/11690 | 5/1995 | WIPO | A61K 37/00 |
| WO 85/02772 | 7/1995 | WIPO | A61K 49/00 |
| WO 95/28838 | 11/1995 | WIPO | A01N 37/46 |
| WO 95/28920 | 11/1995 | WIPO | A61K 31/19 |
| WO 96/12473 | 5/1996 | WIPO | A61K 9/16 |
| WO 96/12474 | 5/1996 | WIPO | A61K 9/16 |
| WO 96/12475 | 5/1996 | WIPO | A61K 9/16 |
| WO 96/21464 | 7/1996 | WIPO | A61K 39/00 |
| WO 96/30036 | 10/1996 | WIPO | A61K 38/00 |
| WO 96/33699 | 10/1996 | WIPO | A61K 9/16 |
| WO 96/39835 | 12/1996 | WIPO | A01N 43/50 |
| WO 96/40070 | 12/1996 | WIPO | A61K 9/14 |
| WO 96/40076 | 12/1996 | WIPO | A61K 9/16 |
| WO 97/10197 | 3/1997 | WIPO | C07C 51/10 |
| WO 97/31938 | 9/1997 | WIPO | C07K 5/00 |
| WO 97/36480 | 10/1997 | WIPO | A01N 37/12 |
| WO 97/47288 | 12/1997 | WIPO . | |

OTHER PUBLICATIONS

Gurrieri, S. et al. (1973) *Thermochimica Acta,* vol. 7, pp. 231–239.

Harada, K. et al. (1979) *BioSystems,* vol. 11, pp. 47–53.

Harada et al., (1960) *Archives of Biochemistry and Biophysics,* vol. 86, pp. 274–280.

Hare (1970) *Etude Cenetique De La Polycondensation Thermique D'χ–Amino Acides,* vol. 45, pp. 330–339.

Heinrich, M.R. et al. (1969) *Archives of Biochemistry and Biophysics,* vol. 130, pp. 441–448.

Heinz, B. et al. (1981) *BioSystems,* vol. 14, pp. 33–40.

Hennon, G. et al. (1975) *Biochimie,* vol. 57, pp. 1395–1396.

Hsu, L.L. et al. (1976) *BioSystems,* vol. 8, pp. 89–101.

Hsu, L.L. et al. (1971) *Currents in Modern Biology,* vol. 4, pp. 12–25.

Ishima, Y. et al. (1981), *BioSystems,* vol.14, pp. 243–251.

Jackson et al. (1991) "Pharmacological . . . ", *J. Pharm. & Exp. Thera.,* vol. 261, No. 1, pp. 546–552.

Jungck, J.R. et al. (1973) *Naturwissenschaften,* vol. 60, pp. 425–427.

Kokufuta, E. et al. (1984) *BioSystems,* vol. 16, pp. 175–181.

Krampitz, G. et al. (1967) *Naturwissenschaften,* pp. 516–517.

Krampitz, G. et al. (1968) *Naturwissenschaften,* pp. 345 and 346.

Krampitz, G. et al. (1966) *Naturwissenschaften,* pp. 7 and 8.

Lacey, Jr., J.C. et al. (1979) *BioSystems,* vol. 11, pp. 9–17.

Lacey, Jr., J.C. et al. (1979) *BioSystems,* vol. 11, pp. 1–7.

Martinez Luque–Romero, M. et al. (1986) *BioSystems,* vol. 19, pp. 267–272.

Masinovsky, Z. et al. (1989) *BioSystems,* vol. 22, pp. 305–310.

Matsuno, K. (1982) *BioSystems,* vol. 15, pp. 1–11.

Matsuno, K. (1984) *BioSystems,* vol. 17, pp. 11–14.

Matsuno, K. (1981) *BioSystems,* vol. 14, pp. 163–170.

McAlhaney, W.W. et al. (1976) *BioSystems,* vol. 8, pp. 45–50.

Melius, P. et al. (1987) *BioSystems,* vol. 20, pp. 213–217.

Melius, P. et al. (1975) *Bioorganic Chemistry,* vol. 4, pp. 385–391.

Melius, P. (1979) *BioSystems,* vol. 11, pp. 125–132.

Miquel, J. et al. (1971) *Currents in Modern Biology,* vol. 3, pp. 299–306.

Nakashima, T. et al. (1980) *J. Mol. Evol.,* vol. 15, pp. 161–168.

Nakashima, T. et al. (1981) *BioSystems,* vol. 14, pp. 151–161.

Novak, V.J.A. (1984) *Origins of Life,* vol. 14, pp. 513–522.

Olafsson, P.G. et al. (1971) *Polymer Letters,* vol. 9, pp. 521–528.

Phillips, R.D. et al. (1974) *Int. J. Peptide Protein Res.,* vol. 6, pp. 309–319.

Przybylski, A.T. et al. (1982) *Die Naturwissenschaften,* vol. 69, pp. 561–563.

Przybylski, A.T. et al. (1984) *Applied Biochemistry and Biotechnology,* vol. 10, pp. 301–307.

Przybylski, A.T. (1985) *BioSystems,* vol. 17, pp. 281–288.

Rohlfing, D.L. (1975) *Origins of Life,* vol. 6, pp. 203–209.

Rohlfing, D.L. (1970) *Science,* vol. 169, pp. 998–1000.

Rohlfing, D.L. (1967) *Archives of Biochemistry and Biophysics,* vol. 118, pp. 468–474.

Rohlfing, D.L. et al. *Catalytic Activities of Thermal Polyanhydro–α–Amino Acids,* pp. 373–418, 1969.

Rohlfing, D.L. et al. (1976) *BioSystems,* vol. 8, pp. 139–145.

Ryan, J.W. et al. (1973) *BioSystems,* vol. 5, pp. 115–118.

Saunders, M.A. et al. (1974) *BioSystems,* vol. 6, pp. 81–92.

Snyder, W.D. et al. (1975) *BioSystems,* vol. 7, pp. 222–229.

Sokol, P.E. (1974) *Journal of the American Oil Chemists'Society,* vol. 52, pp. 101–102.

Tschager et al. (1988) *Milchwirtschaftliche Berichte,* vol. 95, pp. 79–83.

Vaughan, G. et al. (1987) *BioSystems,* vol. 20, pp. 219–223.

Vol'kenshtein, M.V. (1989) *Molekulyarnaya Biologiya,* vol. 23(1), pp. 23–37.

Waehneldt, T.V. et al. (1968) *Biochim. Biophys. Acta,* vol. 160, pp. 239–245.

Williams et al. (1991) *J. Biol. Chem.,* vol. 266, No. 8, pp. 5182–5190.

Yuki, A. et al. (1969) *Biochemical and Biophysical Research Communications,* vol. 36(4), pp. 657–663.

Zulaski et al. (1983) "New Carboxyalkyl Inhibitors of Brain Enkenphalinase", *J. Med. Chem.,* 26, pp. 60–65.

(1985) *Chemical Abstracts,* vol. No. 105(1), Abstract No. 12027p.

(1985) *Chemical Abstracts,* vol. No. 102(6), Abstract No. 50870d.

*Chemical Abstract,* vol. 80(9) Abst. No. 52392a.

Bergeron, Raymond J., et al. (1994) "Macromolecular Self–Assembly of Diketopiperazine Tetrapeptides", *Journal of the American Chemical Society,* vol. 116, pp. 8479–8484.

Bergeron, Raymond J., et al. (1993) "A Comparative Study of the Iron–Clearing Properties of Desferrithiocin Analogues With Desferrioxamine B in a Cebus Monkey Model", *Blood,* vol. 81, No. 8, pp. 2166–2173.

Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood,* vol. 79, No. 7, pp. 1882–1890.

Bergeron, Raymond J., et al. (1991) "Evaluation of Desferrithiocin and Its Synthetic Analogs as Orally Effective Iron Chelators", *Journal of Medicinal Chemistry,* vol. 34, No. 7, pp. 2072–2078.

Bergeron, Raymond et al., "A Comparative Evaluation of Iron Clearance Models", *Annals New York Academy of Sciences*, pp. 278–393, Mar. 13–15, 1990.

Andriuoli, G., et al. (1990), *Haemostasis* 20 (suppl. 1):154–158.

Caramazza, I., et al. (1991), *Thrombosis Research* 62:785–789.

Guarini, S., et al. (1983), *Experimentia* 41:350–352.

Guarini, S., et al. (1985), *Pharmacological Research Communications* 17(8):685–697.

Dal Pozzo, A., et al. (1989), *Thrombosis Research* 56:119–124.

Gelb, R., et al (1983), *Lite Sciences* 33(1):83–85.

Watterberg et al. (1988), *Pediatric Research*, vol. 23, No. 4, part 2, p. 570A, col. 1, abstract No. 2209.

Bernstein (1985), *Chest* 87(1):68S–73S.

Damge et al. (1988), *Diabetes* 37:246–251.

*Chemical Abstracts*:83 184360k, (1975).

Amino, Y., et al., *Chem. Pharm. Bull.* 36(11):4426–4434 (1988).

Baughman, R.A. et al., *Proc. of the 6th Inter'l. Symp. on Recent Advs. in Drug Delivery Systems, Ctr. for Controlled Chem. Delivery, University of Utah*, Feb. 22–25, 1993, Salt Lake City, UT, pp. 179–180 "Method for Assessing The Stability of Proteinoid Microspheres".

Haas, S. et al., "Assessment Of Stability Of Proteinoid Microspheres", *Proceed. Intern. Symp. Control. Rel. Bioact. Mater., 20 (1993)*, Controlled Release Society, Inc.

X. Ma, et al., *Proceed. Intern. Symp. Control. Rel. Bioact. Mater., 20 (1993)*, Controlled Release Society, Inc. "In Vitro Mechanistic Investigation of the Proteinoid Microsphere Oral Delivery System".

Yen, H.–R H., et al., "Adsorption of Sulforhodamine 101 on Proteinoid Microspheres" *Proceed. Intern. Symp. Control. Rel. Bioact. Mater., 20 (1993)*, Controlled Release Society, Inc.

Presented at *"IBC Rational Drug Design Conference"*, San Diego, Calif.—Dec. 1994.

Leone–Bay et al., Presented at *"Winter Conference on Medicinal and Bioorganic Chemistry"* Steamboat Springs, Colorado—Feb. 1995 "Microsphere Formation and Drug Delivery in a Series of Derivatized Amino Acids".

Santiago et al., *Pharm. Res.* 11: 1994, p.S–298 "Oral Delivery of Heparin Microspheres made with Modified Amino Acids".

Leone–Bay et al., *Pharm. Res.* 11: 1994, p.S–121 "Oral Delivery of Heparin using Acylated Amino Acids".

Sarubbi et al., *Pharm. Res.* 11: 1994, p.S–299 "Oral Calcitonin Delivery using the PODDS Technology".

Leipold et al., *Pharm. Res.* 11: 1994, p.S–298 "Oral Delivery of Interferon in Rats and Primates".

Santiago et al., *Pharm. Res.* 11: 1994, p.S–298 "Evaluation in Rats of Vehicles for the Oral Delivery of Low Molecular Weight Heparin".

X. Ma et al., PDD 7303 *Pharmaceutical Research* 9(10):S–244, 1992 (Oct. Supplement).

Milstein et al., *Symposia Abstracts*. AAPS Annual Meeting, San Antonia, TX, Nov. 15–19, 1993.

Santiago et al. "Initial Studies In The Assessment of Proteinoid Microsphere Activity" *Proceed. Intern. Symp. Control. Rel. Bioact. Mater., 20 (1993)*, Controlled Release Society, Inc.

Santiago et al. "Oral Immunization of Rats with Influenza Virus M Protein (M1) Microspheres" *Proceed. Intern. Symp. Control. Rel. Bioact. Mater., 19 (1992)*, Controlled Release Society, Inc., p. 116–117.

Santiago et al. "Proteinoid Microspheres For The Oral Delivery of Heparin" *Proceed. Intern. Symp. Control. Rel. Bioact. Mater., 19 (1992)*, Controlled Release Society, Inc. p. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater., 19 (1992)*, Controlled Release Society, Inc. p. 516–517.

Doris K. Chiappetta, *Eastern Analytical Symposium*, Nov. 17, 1992 "Solutions for Problems in Bioanalysis".

Elizabeth A. Harris. M.S., *Eastern Analytical Symposium*, Nov. 17, 1992 "Solutions for Problems in Bioanalysis".

*AAPS 6TH Ann. Meeting and Expo.*, "Proteinoids—A Novel Drug Delivery System" Nov. 19, 1992, p.33.

Milstein et al., "Efficient Oral Delivery Of Monoclonal Antibodies By Proteinoid Encapsulation" *The 1993 Miami Bio/Technology Winter Symposium—Advances in Gene Technology: Protein Engineering and Beyond*, Jan. 17–22, 1993.

Xinghang Ma, et al. "Stability Study of Drug–loaded Proteinoid Microsphere Formulations during Freeze–drying" *Journal of Drug Targeting, 1994*, vol. 2, pp 9–21.

Baughman et al., "Screening Candidate Microsphere Formulations By Incubating In Simulated Digestive Fluids" *Proc. of the 6th Intern'l. Sympo. on Recent Advances in Drug Delivery Systems*, Ctr. for Controlled Chem. Delivery, University of Utah, Feb. 22–25, 1993, pp. 181–182.

Robert O. Dillman, M.D., *Annals of Internal Medicine* 1989:111 pp. 592–600, "Monoclonal Antibodies for Treating Cancer".

Brendan D. Curti, *Critical Reviews in Oncology/Hematology*, 1993: 14 pp. 29–39 "Physical barriers to drug delivery in tumors".

V. Hird et al, *Genes and Cancer*, edited by Desmond Carney & Karol Sikora, pp.183–189, Immunotherapy with Monoclonal Antibodies.

Michael E. Osband et al., *Immunology Today*, vol. 11, No.6 1990, pp. 193–195, "Problems in the investigational study and clinical use of cancer immunotherapy".

William J. Harris, *Tibtech* Feb. 1993 vol.11, pp. 42–44 "Therapeutic antibodies—the coming of age".

Thomas A. Waldmann, *Science*, Jun. 21, 1991, 252:1657–1662, "Monoclonal Antibodies in Diagnosis and Therapy".

*Chemical Abstracts*, 76(14):72994u, (1971).

*Chemical Abstracts*, 84(7):44660d, (1975).

*Chemical Abstracts*, 86(16):107529g, (1976).

*Chemical Abstracts*, 112(15):134663h, (1989).

*Chemical Abstracts*, 114(22):214519x, (1990).

J. Györe et al., *Thermal Analysis*, vol. 2—Proceeding Fourth ICTA Budapest 1974, p.387–394.

*Chemical Abstracts*, 99(19) 158832b, (1982).

*Derwent Abstracts*, JP 67008622, (1967).

*Journal of Medicinal Chemistry*, vol. 38, No. 21, pp. 4257–4262, (1995), "Microsphere Formation in a Series of Derivatized α–Amino Acids: Properties, Molecular Modeling, and Oral Delivery of Salmon Calcitonin".

Andrea Leone–Bay et al., *Journal of Medicinal Chemistry*, vol. 38, No. 21, pp.4263–4269, (1995), "N–Acylated α–Amino Acids as Novel Oral Delivery Agents for Proteins".

*The Extra Pharmacopoeia*, Thirtieth Edition, pp. 325–326, (1993).

Stephen J. Douglas et al., *Chemistry and Industry*, vol. 22:748–751, 1985.

C.A. Finch, *Chemistry and Industry*, vol. 22:752–756, 1985.

John A. Butera et al., *J. Med. Chem.*, vol. 34:3212–3228, 1990.

Madeline G. Cimini et al., *Ann. Report in Med Chem.*, vol. 27:89–98., 1992.

Bernadette Earley et al., *Brain Research*, vol. 546:282–286, 1991.

John W. Ellingboe et al., *J. Med Chem.*, vol. 35:705–716, 1992.

William C. Lumma et al., *J. Med Chem.*, vol. 30:758–763, 1987.

Joseph J. Lynch et al., *J. of Pharm. and Exp. Therap.*, vol. 269:541–554, 1994.

Kiyoshi Matsuno et al., *Brain Research*, vol. 575:315–319, 1992.

Thomas K. Morgan et al., *J. Med. Chem.*, vol. 33:1091–1097, 1990.

Hitoshi Oinuma et al., *J. Med. Chem.*, vol. 33:903–905, 1990.

Tadimeti S. Rao et al., *Molecular Pharmacology*, vol.37:978–982, 1990.

Asaji Kondo, *Microcapsule Processing and Technology*, pp. 154–165, 1979.

G. Pastores et al., *J. Liquid Chromatography*, 18(15):3049–3059, 1995.

D. Sinha et al., *J. Bio. Chem.*, 260(19):10714–10719. 1985.

E. Franssen et al., *J. Med. Chem.*, 35:1246–1259, 1992.

*Chemical Abstracts*, 99(23):191473h, Dec. 5, 1983.

R. Langer, *Science*, 249:1528, Sep. 28, 1990.

M. Alonso et al., *Vaccine*, 12:299, 1994.

A. Leone–Bay et al., *J. Med. Chem.*, 39:2571–2578, 1996.

R. Thompson, *Biochemistry*, 12:47–51, 1973.

S. Thompson, *J. Med. Chem.*, abstract, 86:174780, 1986.

METHOD FOR PREPARING ω-AMINOALKANOIC ACID DERIVATIVES FROM CYCLOALKANONES

This application is the U.S. national phase of International Application No. PCT/US96/14805, filed Sep. 10, 1996, published as WO 97/10197 on Mar. 20, 1997 which claims priority on the basis of U.S. provisional patent application Ser. No. 60/003,508, filed Sep. 11, 1995. This application claims priority pursuant to 35 U.S.C. §119 from U.S. provisional application Ser. No. 60/003,508, the entire disclosure of which is hereby incorporated by reference.

FIELD OF THE INVENTION

The present invention relates to a method for the preparation of ω-aminoalkanoic acids, N-Boc protected ω-aminoalkanoic acids, and Boc-amino acid coupled ω-aminoalkanoic acids.

BACKGROUND OF THE INVENTION

ω-Aminoalkanoic acids have a wide variety of applications. One such use is as spacer molecules in solid phase peptide synthesis (SPPS). These spacer molecules serve to distance the growing peptide chains from the solid resin support allowing the supported biopolymers to be more accessible for subsequent chemical reactions. *J. Org. Chem.*, 41, page 1350, (1976). Incorporation of such spacers can be important in the preparation of combinatorial libraries wherein large enzymes or antibodies are frequently used to assess the in-vitro activities of the pendant peptides. Minimization of restrictions exerted by the resin allows a more effective interaction between the protein and peptide, *Immunomethods*, 1, page 11, (1992).

For example, substituted 6-aminocaproic acid derivatives have been used to induce and maintain conformational rigidity in peptide fragments. The resulting cyclic peptidomimetic compounds have β-turn structures. *J. Am. Chem.*, 117, page 5169, (1995).

The ω-aminoalkanoic acids are also used in the covalent modification of antigenic peptides with lipophilic moieties such as aminohexadecanoic acid or lauric acid to enhance immunogenicity. For example, a laurylpetide adjuvant can be coupled to a 16 amino acid peptide from the V3 loop of the third hypervariable domain of the HIV-1 to envelope glycoprotein gp 120. This adjuvant-linked peptide stimulated elevated immune responses when compared to the peptide alone. *J. Med. Chem.*, 38, page 459, (1995).

The ω-aminoalkanoic acids can also serve as useful synthetic "handles" for these adjuvants since these acids contain both amino and carboxylic termini which can be further derivatized.

Because of the many uses for ω-aminoalkanoic acids, there is a need in the art for a simple, inexpensive route to prepare these ω-aminoalkanoic acids and their derivatives. A number of methods for the preparations of ω-aminoalkanoic acids have been reported. The amine group on the ω-aminoalkanoic acids can be introduced by first converting a ketone to an oxime using hydroxylamine sulfonic acid. The ω-hydroxyimino acids formed are then reduced using Raney nickel to provide ω-aminoalkanoic acids. (French Patent 1,349,281, Jan. 7, 1964). The preparation of ω-aminoalkanoic acids by reduction of an organic acid with a terminal nitrile to an amine, with lithium aluminum hydride, has also been reported. The nitriles were prepared by conversion of an acid having a terminal group such as a halogen to a nitrile group. *Chem. Tech.*, 8, page 187, (1956). Other methods require formation of an anhydride from an organic diacid followed by opening the anhydride with an azide. The intermediate compound was rearranged via a Schmidt rearrangement at an elevated temperature (50–60°). *Chem & Pharm. Bull.*, 7, page 99, (1959). Cyclic anhydrides have been opened with concentrated ammonium hydroxide followed by warming to about 50° and addition of sodium hydroxide to provide the corresponding half amide. The half-amide can be converted to the corresponding ω-aminoalkanoic acid by Hofmann rearrangement using aqueous base and bromine. *Chem. Ber.*, 89, page 117, (1956).

Boc protected ω-aminoalkanoic acids have been prepared from lactams that have been previously acylated with a t-butyloxycarbonyl acylating agent. The N-acylated lactam product can be treated with a base in aqueous tetrahydrofuran to provide the N-butoxycarbonyl ω-aminoalkanoic acids by hydrolysis. However, chromatographic purification of the N-butoxycarbonyl lactams is usually required. *J. Org. Chem.*, 48, page 2424, (1983).

Aubé et al. recently reported the synthesis Boc protected peptides of methyl substituted 6-aminohexanoic acid. A lactam was prepared and opened with hydrochloric acid solution. The ring opened lactam can be coupled to the peptide. However, this procedure required protection of the carboxyl terminus of the 6-aminohexanoic acids as a methyl esters before coupling with the peptide. *J. Med. Chem.*, 117, page 5169, (1995).

Each of the preceding methods have difficulties such as low yields, the need for purification, expensive reagents and/or scale-up problems.

SUMMARY OF THE INVENTION

A convenient synthetic route to acylated ω-aminoalkanoic acids N-Boc protected ω-aminoalkanoic acids or Boc-amino acid coupled ω-aminoalkanoic acids is disclosed. The method of the invention provides high purity compounds that generally do not require further purification.

The invention provides a method for the preparation of a compound having the formula:

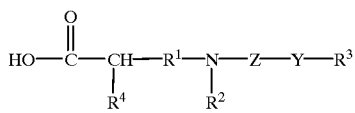

wherein
- Y is carbonyl, $C_1$–$C_4$ alkyl carbonyl, oxycarbonyl, $C_1$–$C_4$ alkyl oxycarbonyl, or $SO_2$;
- Z is a bond, an amino acid residue, a peptide residue, or a poly amino acid residue;
- $R^1$ is $C_1$–$C_{24}$ alkyl, $C_2$–$C_{20}$ alkenyl, or $C_2$–$C_{20}$ alkynyl;
- $R^2$ is hydrogen, $C_1$–$C_4$ alkyl, $C_2$–$C_4$ alkenyl, cycloalkyl, heterocyclic, aryl, or heteroaryl; and
- $R^3$ is $C_1$–$C_7$ alkyl, $C_3$–$C_{10}$ cycloalkyl, phenyl, aryl, thienyl, pyrrolo, or pyridyl, where $R^3$ is optionally substituted by one or more $C_1$–$C_5$ alkyl, $C_2$–$C_4$ alkenyl group, $C_1$–$C_5$ alkoxy, $C_1$–$C_5$ alkylamino, di-$C_1$–$C_5$ alkylamino halogen, OH, $NO_2$, $NH_2$, $SO_2$, COOH, or $SO_3H$;
- $R^4$ is $C_1$–$C_7$ alkyl, $C_3$–$C_{10}$ cycloalkyl, aryl, thienyl, pyrrolo, or pyridyl, where $R^4$ is optionally substituted by one or more $C_1$–$C_5$ alkyl group, $C_2$–$C_4$ alkenyl group, F, Cl, OH, $SO_2$, COOH, or $SO_3H$.

The method comprises:
(a) reacting a cycloalkanone compound having the formula:

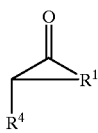

with formic acid and hydroxylamine-O-sulfonic acid to provide a lactam having the formula:

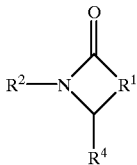

(b) reacting the lactam with an aqueous base to form an amine salt; and
(c) acylating the amine salt with a compound having the formula $R^3—Y—Z—X$ wherein $R^1$, $R^2$, $R^3$, $R^4$, Z and Y are as defined above and X is a leaving group.

Advantages of the present invention include the use of easy to prepare, and/or inexpensive raw materials. The method of the present invention is cost effective, simple to perform, and amenable to industrial scale up for commercial production.

DETAILED DESCRIPTION OF THE INVENTION

The present invention provides a convenient synthetic route to ω-aminoalkanoic acids, acylated ω-aminoalkanoic acids N-Boc protected ω-aminoalkanoic acids and Boc-amino acid coupled ω-aminoalkanoic acids. The method described herein provides syntheses of ω-aminoalkanoic acid analogs that generally do not require further purification or protection of the carboxyl function. These compounds are prepared with less handling. In addition, by avoiding hydrogenation, azide or bromine related rearrangements, the syntheses are very readily amenable to scale-up.

The compounds have been prepared amounts up to 1 kg with high purity. Consequently, these compounds are suitable for solution or solid phase peptide synthesis using BOC chemistry. Homologues with variable chain length maybe prepared by using different cycloalkanones.

The method of the invention provides a preparation of compounds having the formula:

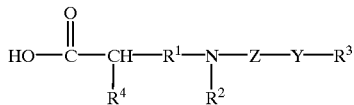

wherein
Y is carbonyl, $C_1$–$C_4$ alkyl carbonyl, oxycarbonyl, $C_1$–$C_4$ alkyl oxycarbonyl, or $SO_2$;
Z is a bond, an amino acid residue, a peptide residue, or a poly amino acid residue;

$R^1$ is $C_1$–$C_{24}$ alkyl, $C_2$–$C_{20}$ alkenyl, or $C_2$–$C_{20}$ alkynyl;
$R^2$ is hydrogen, $C_1$–$C_4$ alkyl, $C_2$–$C_4$ alkenyl, cycloalkyl, heterocyclic, aryl, or heteroaryl; and
$R^3$ is $C_1$–$C_7$ alkyl, $C_1$–$C_7$ alkoxy, $C_3$–$C_{10}$ cycloalkyl, phenyl, aryl, thienyl, pyrrolo, or pyridyl, where $R^3$ is optionally substituted by one or more $C_1$–$C_5$ alkyl, $C_2$–$C_4$ alkenyl group, $C_1$–$C_5$ alkoxy, $C_1$–$C_5$ alkylamino, di-$C_1$–$C_5$ alkylamino halogen, OH, $NO_2$, $NH_2$, $SO_2$, COOH, or $SO_3H$;
$R^4$ is $C_1$–$C_7$ alkyl, $C_3$–$C_{10}$ cycloalkyl, phenyl, aryl, thienyl, pyrrolo, or pyridyl, where $R^4$ is optionally substituted by one or more $C_1$–$C_5$ alkyl group, $C_2$–$C_4$ alkenyl group, $C_1$–$C_5$ alkoxy, $C_1$–$C_5$ alkylamino, di-$C_1$–$C_5$ alkylamino halogen, OH, $NO_2$, $NH_2$, $SO_2$, COOH, or $SO_3H$.

The method comprises:
(a) reacting a cycloalkanone compound having the formula:

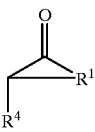

with formic acid and hydroxylamine-O-sulfonic acid to provide a lactam having the formula:

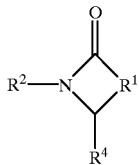

(b) reacting the lactam with an aqueous base to form an amine salt; and
(c) acylating the amine salt with a compound having the formula $R^3—Y—Z—X$ wherein $R^1$, $R^2$, $R^3$, $R^4$, Z, and Y are as defined above and X is a leaving group.

In a preferred embodiment the Y is oxycarbonyl, and Z is a bond or an amino acid residue; $R^1$ is alkyl having from 5 to 9 carbon atoms; $R^2$ and $R^4$ are hydrogen; and $R^3$ is $C_1$–$C_4$ alkyl or phenyl. The most preferred $R^3$ is tert-butyl.

Compounds useful for acylating or sulfonating the amine salts of the invention have the formula $R^3—Y—Z—X$ wherein:
$R^3$ is $C_1$–$C_7$ alkyl, $C_3$–$C_{10}$ cycloalkyl, phenyl, aryl, thienyl, pyrrolo, or pyridyl, where $R^3$ is optionally substituted by one or more $C_1$–$C_5$ alkyl, $C_2$–$C_4$ alkenyl group, $C_1$–$C_5$ alkoxy, $C_1$–$C_5$ alkylamino, di-$C_1$–$C_5$ alkylamino halogen, OH, $NO_2$, $NH_2$, $SO_2$, COOH, or $SO_3H$;
Y is carbonyl, alkyl carbonyl, araalkyl carbonyl, oxycarbonyl, alkyl oxycarbonyl, araalkyl oxycarbonyl, or $SO_2$; Z is an amino acid residue, a peptide residue, or a poly amino acid residue and X is a leaving group.

Typical leaving groups include, but are not limited to, halogens such as, for example, chlorine, bromine, and iodine. Additionally, the corresponding anhydrides can be used as acylating agents.

A preferred compound for acylating the amine salt is a compound having the formula (CH$_3$)$_3$C—O—CO—Z—X where Z is a bond or an amino acid residue, X is a leaving group. Examples of preferred acylating compounds include compounds such as, for example, ((CH$_3$)$_3$COCO)$_2$O and Boc protected amino acid succinate esters. A preferred acylating group where Z is an amino acid residue is a Boc protected amino acid-O-succinate ester such as, for example, Boc-phenyl alanyl-O-succinate ester.

An amino acid residue is an amino acid which has a hydrogen atom removed from either or both the amine or acid end of the molecule. An amino acid is any carboxylic acid having at least one free amine group and includes naturally occurring and synthetic amino acids. The invention includes amino acid residues where the amino acid residue is a single amino acid, a peptide, and a poly amino acid A poly amino acid residue is a poly amino acid which has a hydrogen atom removed from either or both of an amine or acid group of the molecule. Poly amino acids are either peptides or two or more amino acids linked by a bond formed by other groups which can be linked, e.g. an ester, anhydride, or an anhydride linkage.

A peptide residue is an peptide which has a hydrogen atom removed from either or both the amine or acid end of the molecule. Peptides are two or more amino acids joined by a peptide bond. Peptides can vary in length from dipeptides with two amino acids to poly peptides with several hundred amino acids. See *Chambers Biological Dictionary*, editor Peter M. B. Walker, Cambridge, England: Chambers Cambridge, 1989, page 215.

The method of the invention is illustrated by the following scheme:

aqueous base, such as sodium hydroxide, to provide the amine salt, Compound 3.

The Boc protected 8-amino caprylic acid, Compound 4 was prepared from a solution of the amine salt, 5, by the addition of di-t-butyl-dicarbonate. A 63% yield of 8-(t-butoxycarbonylamino)caprylic acid, 4, was isolated based on the lactam, 2.

Attempts to acylate the free amine of 8-amino caprylic acid, with an O-succinic (-OSu) ester of a Boc-amino acid failed. The major product was the parent Boc-amino acid resulting from hydrolysis of the O-succinic ester. When the using the amine salt for the acylation with the Boc-Phe-OSu this problem was overcome. The amount of hydrolysis of the O-succinic ester was reduced and a 43% yield (over two steps) of the desired (N-t-butoxycarbonylphenylalanyl)-8-amino caprylic acid, Compound 5 was obtained.

Thus, the N-Boc protected or Boc-amino acid coupled ω-aminoalkanoic acids were readily prepared using the method of the invention.

DESCRIPTION OF THE PREFERRED EMBODIMENTS

The following examples illustrate the invention without limitation. All parts are given by weight unless otherwise indicated.

EXAMPLE 1

Synthesis of 2-Azacyclononanone (2)

A 5 L three-neck round bottom flask was fitted with a heating mantle, an overhead mechanical stirrer, an addition funnel, and a thermometer. The reaction was performed under an argon atmosphere. Hydroxylamine-O-sulfonic acid (196.7 g, 1.74 moles, 1.10 equiv.) and formic acid (1 L) were charged into the round bottom flask and stirred to form a white slurry. A solution of cyclooctanone (200.0 g 1.58

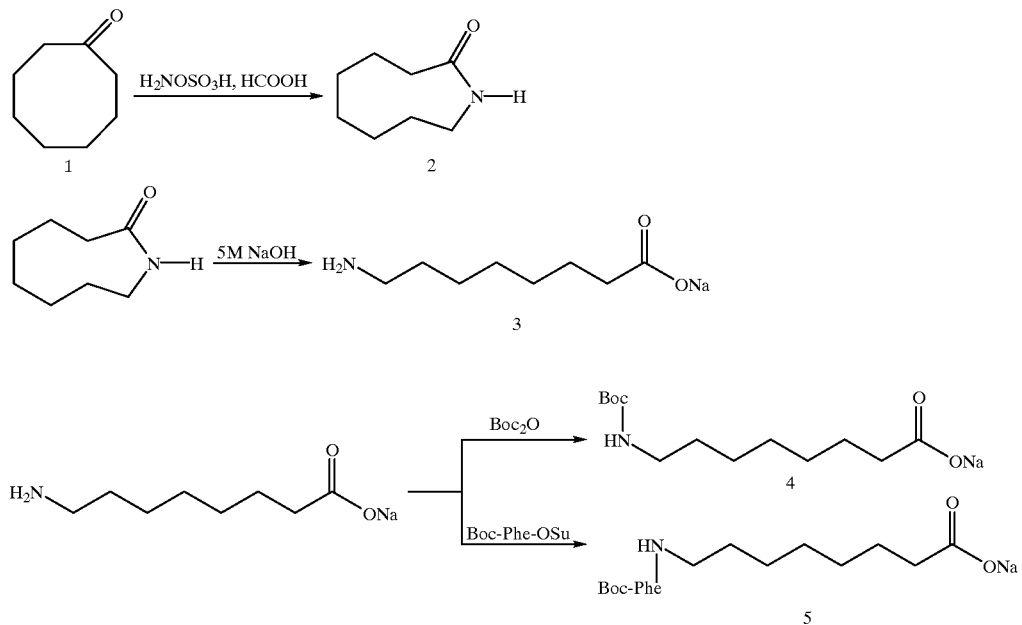

The cyclooctanone, Compound 1, is treated with formic acid and hydroxylamine-O-sulfonic acid to provide the lactam, Compound 2. The lactam is then hydrolyzed with an moles, 1.0 equiv.) in formic acid (600 mL) was added dropwise to the white slurry via the addition funnel. After the addition, the addition funnel was replaced by a reflux condenser, and the reaction was heated to reflux (internal temperature about 105° C.) for 1 hour to give a brown solution. After the solution was cooled to room temperature, it was poured into a mixture of saturated aqueous ammonium chloride (1.5 L) and water (1.5 L). The aqueous mixture was extracted with chloroform (3×1200 mL). The combined chloroform layers were transferred into a beaker, and saturated sodium bicarbonate (2 L) was added slowly. The chloroform layer was then separated, dried over anhydrous sodium sulfate, and evaporated under reduced pressure to afford brown oil. The oil was placed in a 500 mL round bottom flask with a agnetic stirrer. The round bottom flask was placed in a silicon oil bath and was fitted with a short path vacuum distillation head equipped with a thermometer. A Cow-type receiver was connected to three 250 mL flasks. 2-Azacyclononanone (145 g, 65%, mp 64–69° C.) was obtained by vacuum distillation (fraction with head temperature range from 80 to 120° C. at pressures between 3.0 and 3.4 mmHg).

EXAMPLE 2

Sodium 8-Aminocaprylate (3)

A 5 L three-neck round bottom flask was fitted with a heating mantle, an overhead mechanical stirrer, a reflux condenser, and a thermometer. A suspension of 2-azacyclononanone (83 g, 0.59 moles, 1.0 equiv.) in 5 M aqueous sodium hydroxide (650 mL, 3.23 moles, 5.5 equiv.) was charged into the round bottom flask. The mixture was heated to reflux (internal temperature about 110° C.) for 4 hours to yield a clear yellow solution. The heating mantle and reflux condenser were removed. After the solution cooled to room temperature, it was diluted with water (650 mL) and cooled further in an ice bath.

EXAMPLE 3

8-(tert-Butoxycarbonylaminolcaprylic acid (4)

To a 250 mL three-neck round bottom flask equipped with a magnetic stirrer and an addition funnel, was added a solution of sodium 8-aminocaprylate (0.45 mmol mL$^{-1}$, 22.5 mmol, 50 mL). The solution was cooled in an ice-bath. Di-tert-butyl dicarbonate (24.75 mmol, 5.40 g, 1.1 equiv) was dissolved in dioxane (50 mL), charged to the addition funnel and added dropwise over 15 min. The mixture was stirred in the ice-bath for 15 min and at ambient temperature for 1 h. The dioxane was evaporated under vacuum, ethyl acetate (30 mL) was added and the heterogeneous solution was cooled in an ice-bath. The solution was acidified with 0.5 M sulfuric acid to pH 2. The ethyl acetate was separated and the aqueous layer was further extracted with 2×30 mL ethyl acetate. The combined organic layers were washed with water (2×30 mL), dried and evaporated. The residue was suspended in hot hexanes (30 mL), followed by dropwise addition of ethyl acetate until a homogenous solution was obtained. The solution was cooled at −5° C. for 4 h. A white solid formed and was collected by filtration to afford 8-(tert-butoxycarbonylamino)caprylic acid (4) (3.67 g, 63%).

Properties are listed below.

Mp 54–55° C.;

IR(KBr); 3362, 2947, 1690, 1520, 1321, 940 cm$^{-1}$.

$^1$H NMR (DMSO-d$_6$)δ: 11.93 (br s, 1H), 8.72 (br s, 1H) 2.87 (q,J=6.54, 12.86 Hz, 2H), 2.19 (t,J=7.33 Hz, 2H), 1.47 (m, 2H), 1.36 (br s, 11H), 1.23 (br s, 6H).

$^{13}$C NMR (DMSO-d$_6$)δ: 174.2 (C), 155.4 (C), 77.1 (C), 39.6 (CH$_2$), 33.5 (CH$_2$), 29.3 (CH$_2$), 28.4 (CH$_2$), 28.3 (CH$_2$), 28.1 (CH/CH$_3$) 26.0 (CH$_2$), 24.3 (CH$_2$).

Anal. Calc. for C$_{13}$H$_{25}$NO$_4$; C, 60.20; H, 9.72; N, 5.40. Found: C, 60.30; H, 9.66; N, 5.33.

EXAMPLE 4

(N-tert-Butoxycarbonylphenylalanyl)-8-aminocaprylic acid (5)

To a 250 mL round bottom flask equipped with an addition funnel was added a solution of sodium 8-aminocaprylate (14.61 mmol, 32.5 mL, 1.2 equiv). The pH of the solution was adjusted to 8.2 by addition of concentrated HCl. The solution was cooled in an ice-bath. Boc-Phe-OSu (12.42 mmol, 4.50 g, 1.0 equiv) was dissolved in 1,4-dioxane (20 mL) and added dropwise. The mixture was stirred in the ice-bath for 30 min and at ambient temperature for 12 h. The solution was acidified with 1 M sulfuric acid (80 mL) and extracted with ether (100+50 mL). The combined organic layers were washed with water (40 mL), dried and evaporated to give a pale yellow oil. The oil was triturated with hexanes (3×50 mL) to afford (N-tert-butoxycarbonylphenylalanyl)-8-aminocaprylic acid (5) (2.17 g, 43%) as a colorless solid.

Properties are listed below.

Mp 96–100° C.

IR (Kbr): 3296, 2980, 1705, 1677, 1631, 1558, 1407 cm$^{-1}$.

$^1$H NMR (DMSO-d$_6$)δ; 12.00 (br s, 1H), 7.82 (t, J=5.34 Hz, 1H), 7.18 (m, 5H), 6.86 (d,J=8.58 Hz, 1H), 4.09 (M, 1H), 3.00 (m, 2H), 2.88 (dd, J=5.09, 13.64 Hz, 1H), 2.72 (dd,J= 9.72, 13.51 Hz, 1H), 2.17 (t,J=7.31 Hz, 2H), 1.47 (m,2H), 1.29 (2 overlapped br s, 19H).

$^{13}$CNMR (DMSO-d$_6$)δ: 174.2 (C), 171.0 (C), 137.9 (CH/CH$_3$), 129.0 (CH/CH$_3$), 127.8 (CH/CH$_3$), 125.9 (CH/CH$_3$), 77.8 (C), 55.54 (CH/CH$_3$), 38.3 (CH$_2$), 37.7 (CH$_2$), 33.5 (CH$_2$), 28.8 (CH$_2$), 28.3 (2×CH$_2$), 27.9 (CH/CH$_3$), 26.0 (CH$_2$), 24.3 (CH$_2$).

MS (FAB, thioglycerol): 407 (13,M$^{+1}$+1), 351 (13), 307 (100), 289 (5), 261 (11). HRMS (EI) calc. for C$_{22}$H$_{35}$N$_2$O$_5$ (M$^{+1}$+1) 407.2546, found 407.2562; calc. for C$_{22}$H$_{34}$N$_2$O$_5$ (M$^{+1}$) 406.2468, found 406.2476.

Anal. Calc. for C$_{22}$H$_{34}$N$_2$O$_5$; C, 65.00; H, 8.43; N, 6.89. Found: C, 64.43; H, 8.24; N, 6.73.

EXAMPLE 5

Synthesis of 2-Azacyclohexanone

Following the procedure of Example 1 and substituting cyclopentanone for cyclooctanone, 2-azacyclohexanone is prepared.

EXAMPLE 6

Sodium 6-aminopentanoate

Following the procedure of Example 2 and substituting 2-azacyclohexanone for 2-azacyclononanone, sodium 6-aminopentanoate is prepared.

EXAMPLE 7

6-(tert-Butoxycarbonylamino)pentanoic acid

Following the procedure of Example 3 and substituting sodium 6-aminopentanoate for sodium 8-aminocaprylate, 6-(tert-butoxycarbonylmino)pentanoic acid is prepared.

EXAMPLE 8

(N-tert-Butoxycarbonylphenylalanyl)-6-aminnopentanooc acid

Following the procedure of Example 4 and substituting sodium 6-aminopentanoate for sodium 8-aminocaprylate, (N-tert-butoxycarbonylhenylalanyl)-6-aminopentanoic acid is prepared.

EXAMPLE 9

(N-tert-Butoxycarbonyl-Phe-Phe)-6-aminopentanoic acid

Following the procedure of Example 4 and substituting sodium 6-aminopentanoate for sodium 8-aminocaprylate and Boc-Phe-Phe-OSu for Boc-Phe-OSu, (N-tert-butoxycarbonyl-Phe-Phe)-6-aminopentanoic acid is prepared.

EXAMPLE 9

(N-tert-Butoxycarbonyl-Phe-Phe)-6-aminopentanoic acid

Following the procedure of Example 4, substituting sodium 6-aminopentanoate for sodium 8-aminocaprylate and Boc-Phe-Phe-OSu for Boc-Phe-OSu, (N-tert-butoxycarbonyl-Phe-Phe)-6-aminopentanoic acid is prepared.

The above mentioned patents, applications, test methods, and publications are hereby incorporated by reference in their entirety.

Many variations of the present invention will suggest themselves to those skilled in the art in light of the above detailed description. All such obvious variations are within the full intended scope of the appended claims.

What is claimed is:

1. A method for preparing a compound having the formula

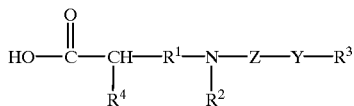

said method comprising:

(a) reacting a cycloalkanone compound having the formula:

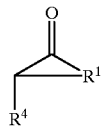

with formic acid an hydroxylamine-O-sulfonic acid to provide a lactam having the formula:

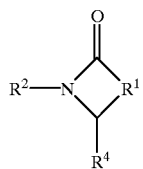

(b) reacting said lactam with an aqueous base to form an amine salt; and (c) acylating said amine salt with a compound having the formula:

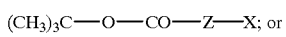

$(CH_3)_3C-O-CO-Z-X$; or

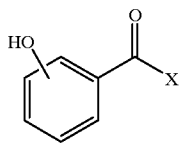

or a Boc protected amino acid succinate ester;
wherein
Y is carbonyl or oxycarbonyl;
Z is a bond or an amino acid residue;
$R^1$ is $C_5-C_9$ alkyl;
$R^2$ is hydrogen;
$R^3$ is tert-butyl or hydroxyphenyl;
$R^4$ is hydrogen; and
X is a leaving group.

2. The method according to claim 1, wherein the amine salt is acylated with a compound having the formula $(CH_3)_3C-O-CO-X$, wherein X is a halide.

3. The method according to claim 1, wherein the amine salt is acylated with a compound having the formula $((CH_3)_3C-O-CO)_2O$.

4. The method according to claim 1, wherein the amine salt is acylated with a Boc protected amino acid succinate ester.

5. The method according to claim 4, wherein the amine salt is acylated with Boc-phenyl alanyl-O-succinate ester.

6. The method according to claim 4, wherein the amine salt is acylated with Boc-phenyl alanyl-phenyl alanyl-O-succinate ester.

7. The method according to claim 1, wherein R1 is alkyl having 6 carbon atoms, Z is a bond, Y is carbonyl, and $R^3$ is 2-hydroxyphenyl.

* * * * *